United States Patent
Vetukuri Vnkv et al.

(10) Patent No.: US 9,765,088 B2
(45) Date of Patent: Sep. 19, 2017

(54) PROCESS FOR THE PREPARATION OF RIFAMYCIN DERIVATIVES

(71) Applicant: Granules India Limited, Hyderabad (IN)

(72) Inventors: Prasada Raju Vetukuri Vnkv, Hyderabad (IN); Goverdhan Gilla, Hyderabad (IN); Ambaiah Boini, Hyderabad (IN); Krishna Prasad Chigurupati, Hyderabad (IN)

(73) Assignee: GRANULES INDIA LIMITED, Hyderabad (IN)

( * ) Notice: Subject to any disclaimer, the term of this patent is extended or adjusted under 35 U.S.C. 154(b) by 0 days.

(21) Appl. No.: 15/304,740

(22) PCT Filed: Apr. 19, 2015

(86) PCT No.: PCT/IB2015/052854
§ 371 (c)(1),
(2) Date: Oct. 17, 2016

(87) PCT Pub. No.: WO2015/159275
PCT Pub. Date: Oct. 22, 2015

(65) Prior Publication Data
US 2017/0037055 A1    Feb. 9, 2017

(30) Foreign Application Priority Data

Apr. 19, 2014 (IN) ............................ 2021/CHE/2014
Dec. 31, 2014 (IN) ............................ 6856/CHE/2014

(51) Int. Cl.
*C07D 498/22*    (2006.01)

(52) U.S. Cl.
CPC ........ *C07D 498/22* (2013.01); *C07B 2200/13* (2013.01)

(58) Field of Classification Search
CPC .................................................... C07D 498/22
See application file for complete search history.

(56) References Cited

U.S. PATENT DOCUMENTS

| 7,045,620 | B2 | 5/2006 | Viscomi et al. |
| 8,158,781 | B2 | 4/2012 | Viscomi et al. |
| 8,193,196 | B2 | 6/2012 | Viscomi et al. |
| 8,633,234 | B2 * | 1/2014 | Rao ...................... C07D 498/22 514/393 |

FOREIGN PATENT DOCUMENTS

WO    2011156897    12/2011

OTHER PUBLICATIONS

International Search Report and Written Opinion for priority PCT Application No. PCT/IB2015/052854 dated Sep. 29, 2015 (9 pages).

* cited by examiner

*Primary Examiner* — Bruck Kifle

(57) ABSTRACT

The present invention relates to an improved and industrially advantageous process for the preparation of Rifaximin with high purity and yield. Particularly, the present invention relates to improved processes for the preparation of Rifaximin from Rifamycin O and S. More particularly the present invention relates to a process for the preparation of Rifaximin through 3-halorifamycin S. The present invention further relates to a novel polymorph of Rifaximin and process for its preparation.

6 Claims, 2 Drawing Sheets

PROCESS FOR THE PREPARATION OF RIFAMYCIN DERIVATIVES

CROSS REFERENCE TO RELATED APPLICATIONS

The present application is the U.S. national stage entry of PCT Application No. PCT/IB2015/052854, filed Apr. 19, 2015, which claims priority to Indian Patent Application No. 2021/CHE/2014, filed Apr. 19, 2014 and Indian Patent Application No. 6856/CHE/2014, filed Dec. 31, 2014, the contents of which are hereby incorporated by reference herein in their entirety.

FIELD OF THE INVENTION

The present invention relates to an improved and industrially advantageous process for the preparation of Rifaximin with high purity and yield. Particularly, the present invention relates to improved processes for the preparation of Rifaximin from Rifamycin O and S. More particularly the present invention relates to a process for the preparation of Rifaximin through 3-halorifamycin S.

The present invention further relates to a novel polymorph of Rifaximin and process for its preparation.

BACKGROUND OF THE INVENTION

Rifaximin is a broad-spectrum antibiotic belonging to the family of Rifamycins and shows its antibacterial activity, in the gastrointestinal tract against localized bacteria that cause infectious diarrhoea, irritable bowel syndrome, small intestinal bacterial overgrowth, Crohn's disease, and/or pancreatic insufficiency.

Rifaximin is sold under the brand name Xifaxan® in US for the treatment of Travellers' diarrhoea and Hepatic Encephalopathy. The chemical name of Rifaximin is (2S,16Z,18E,20S,21S,22R,23R,24R,25S,26S,27S,28E)-5,6,21,23,25-pentahydroxy-27-methoxy-2,4,11,16,20,22,24,26-octamethyl-2,7(epoxypentadeca-[1,11,13]trienimino)benzofuro[4,5-e]pyrido[1,2-a]-benzimidazole-1,15(2H)-dione,25-acetate and the molecular formula is $C_{43}H_{51}N_3O_{11}$ with a molecular weight of 785.9. The structural formula of Rifaximin is:

Formula I

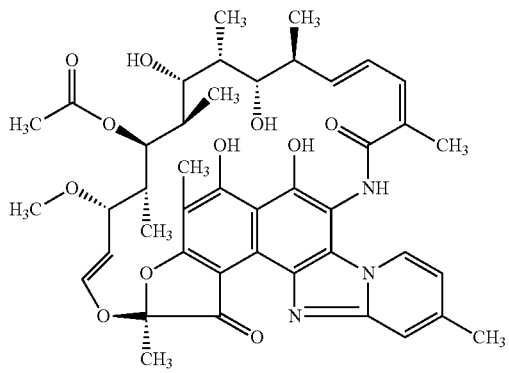

Rifaximin was first described and claimed in Italian patent IT 1154655 and U.S. Pat. No. 4,341,785. These patents disclose a process for the preparation of Rifaximin and a method for the crystallisation thereof. The process for the preparation of Rifaximin is as depicted in scheme I given below:

Scheme-I

Formula II
wherein hal represents halogen atom

Formula III

Rifaximin

U.S. Pat. No. 4,179,438 discloses a process for the preparation of 3-bromorifamycin S which comprises reaction of rifamycin S with at least two equivalents of bromine, per one mole of rifamycin S in the presence of at least one mole of pyridine per each equivalent of bromine and in the presence of ethanol, methanol or mixtures thereof with water at a temperature not above the room temperature. The process is shown in the scheme given below:

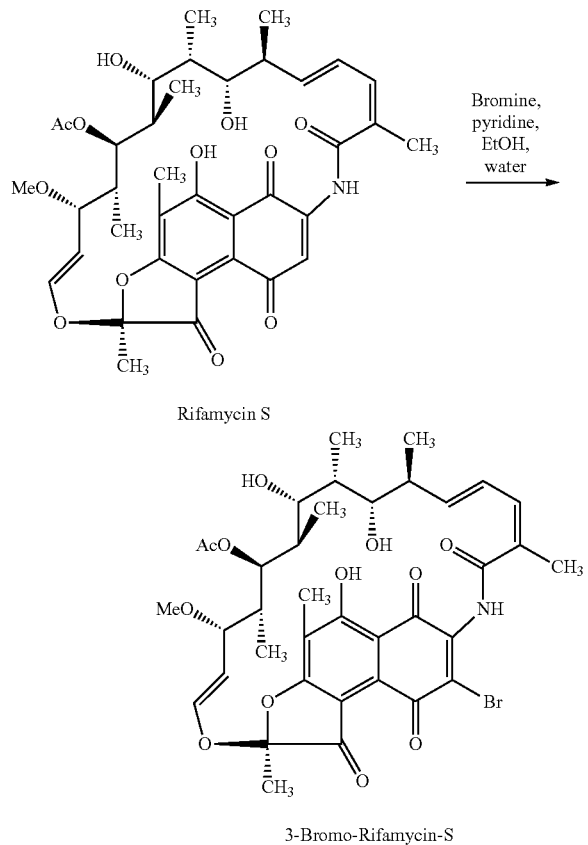

U.S. Pat. No. 4,557,866 discloses a process for one step synthesis of Rifaximin from Rifamycin O, which is shown in scheme II given below:

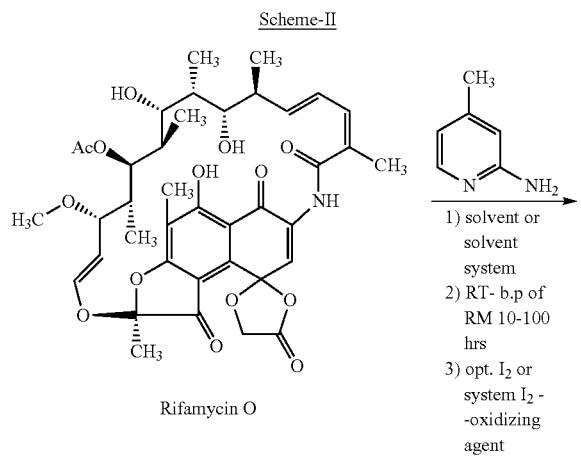

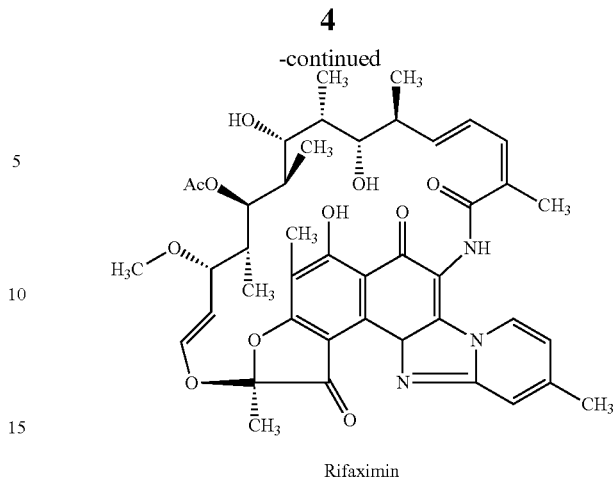

Rifaximin

U.S. '866 patent also discloses purification of Rifaximin by performing crystallization of crude Rifaximin from a 7:3 mixture of ethyl alcohol/water followed by drying both under atmospheric pressure and under vacuum. The crystalline form which is obtained has not been characterized.

U.S. Pat. No. 7,045,620 describes three polymorphic forms α, β and γ of Rifaximin. Form α and β show pure crystalline characteristics while the γ form is poorly crystalline. These polymorphic forms are differentiated on the basis of water content and PXRD. This patent also discloses processes for preparation of these polymorphs which involve use of specific reaction conditions during crystallization like dissolving Rifaximin in ethyl alcohol at 45-65° C., precipitation by adding water to form a suspension, filtering suspension and washing the resulted solid with demineralized water, followed by drying at room temperature under vacuum for a period of time between 2 and 72 hours. Crystalline forms α and β are obtained by immediate filtration of suspension when temperature of reaction mixture is brought to 0° C. and poorly crystalline form γ is obtained when the reaction mixture is stirred for 5-6 hours at 0° C. and then filtered the suspension. In addition to above these forms are also characterized by specific water content. For α form water content should be lower than 4.5%, for β form it should be higher than 4.5% and to obtain γ form, water content should be below 2%.

U.S. Pat. No. 7,709,634 describes an amorphous form of Rifaximin which is prepared by dissolving Rifaximin in solvents such as alkyl esters, alkanols and ketones and precipitating by addition of anti-solvents selected from hydrocarbons, ethers or mixtures thereof.

U.S. Pat. No. 8,193,196 describes two polymorphic forms of Rifaximin, designated δ and ε respectively. Form δ has water content within the range from 2.5 to 6% by weight (preferably from 3 to 4.5%).

U.S. Pat. No. 8,067,429 describes α-dry, β-1, β-2, ε-dry and amorphous forms of Rifaximin.

U.S. Pat. No. 8,227,482 describes polymorphs Form μ, Form π, Form Omicron, Form Zeta, Form Eta, Form Iota and Form Xi of Rifaximin.

International application publications WO 2008/035109, WO 2008/155728, WO 2012/035544, WO 2012/060675, and WO 2012/156533 describes various amorphous or poorly crystalline forms of Rifaximin.

These polymorphic forms are obtained under different experimental conditions and are characterized by XRPD pattern.

The polymorphic forms of Rifaximin obtained from the prior art methods have specific water content. Transition between different polymorphic forms of Rifaximin occurs by drying or wetting of the synthesized Rifaximin. Hence, it is evident from above that Rifaximin can exist in number of polymorphic forms, formation of these polymorphic forms depends upon specific reaction conditions applied during crystallization and drying.

Polymorphism, the occurrence of different crystal forms, is a property of some molecules and molecular complexes. A single molecule may give rise to a variety of polymorphs having distinct crystal structures and physical properties like melting point, X-ray diffraction pattern, infrared absorption fingerprint, and solid state NMR spectrum. One polymorph may give rise to thermal behaviour different from that of another polymorph. Thermal behaviour can be measured in the laboratory by such techniques as capillary melting point, thermogravimetric analysis ("TGA"), and differential scanning calorimetry ("DSC"), which have been used to distinguish polymorphic forms.

The differences in the physical properties of different polymorphs results from the orientation and intermolecular interactions of adjacent molecules or complexes in the bulk solid. Accordingly, polymorphs are distinct solids sharing the same molecular formula yet having distinct advantageous physical properties compared to other polymorphs of the same composition or complex.

Considering the importance of Rifaximin, there exists a need to develop an alternate and improved process for the preparation of Rifaximin with better yield. Further, the process involved should be simple, convenient and cost-effective for large scale production. With a view to find a simple process the present applicant diligently worked and identified a robust and economical process for the preparation of Rifaximin. Further, there also remains a need for polymorphic forms which have properties suitable for pharmaceutical processing on a commercial scale. The inventors of the present invention during their continuous efforts developed a novel polymorphic form of Rifaximin.

OBJECTIVE OF THE INVENTION

The main objective of the present invention is to provide a robust and simple process for the preparation of Rifaximin of Formula I with high yield and high purity.

Another objective of the present invention is to provide an improved process for preparing Rifaximin, which is simple, industrially applicable and economically viable.

Yet another objective of the present invention is to provide novel crystalline Form of Rifaximin which has better solubility, reproducibility, chemical and polymorphic stabilities.

Yet another objective of the present invention is to provide a process for the preparation of Rifaximin novel crystalline Form G.

SUMMARY OF THE INVENTION

Accordingly, the present invention provides a process for the preparation of substantially pure Rifaximin with high yield.

In one aspect, the present provides an improved process for the preparation of Rifaximin which comprises:
a) halogenation of Rifamycin S suitable solvent in the presence of a base, in a
b) optionally isolating 3-halorifamycin S with an acid in a suitable solvent,
c) reacting 3-halorifamycin S with 2-amino-4-methyl pyridine in a suitable solvent,
d) treating the reaction mixture with ascorbic acid,
e) isolating Rifaximin, and
f) optionally purifying Rifaximin obtained in step e) to obtain substantially pure Rifaximin.

In another aspect, the present provides an improved process for the preparation of Rifaximin which comprises:
a) bromination of Rifamycin S in a suitable solvent in the presence of a base,
b) optionally isolating 3-bromorifamycin S with an acid in a suitable solvent,
c) reacting 3-bromorifamycin S with 2-amino-4-methyl pyridine in a suitable solvent,
d) treating the reaction mixture with ascorbic acid,
e) isolating Rifaximin, and
f) optionally purifying Rifaximin obtained in step e) to obtain substantially pure Rifaximin.

In yet another aspect, the present invention relates to an improved process for the preparation of Rifaximin comprising the steps of:
a) reacting rifamycin S with 2-amino-4-methylpyridine in the presence of iodine, acetic acid and solvent acetonitrile at about 30° C. for about 30 hours;
b) obtaining resulted Rifaximin as residue;
c) suspending Rifaximin residue in a solvent or mixture of solvents;
d) heating the suspension of step (c) to about 75° C. to obtain a solution;
e) cooling the solution of step (d) to about 45° C.;
f) optionally seeding the solution of step (e) with seed crystal;
g) cooling the suspension of step (f) further to about 25° C. for about 2 hours;
h) cooling the mass of step (g) further to about 5° C. for about 3 hours;
i) recovering the solid precipitated in step (h) by conventional methods;
j) drying the solid obtained in step (i) at about 50° C. for about 10 hours to afford pure Rifaximin.

In yet another aspect, the present invention relates to a process for the preparation of Rifaximin comprising the steps of:
a) providing rifaximin in a solvent or mixture of solvents; and
b) heating the suspension of step (i) to about 65° C. to obtain a solution; and
c) cooling the solution of step (ii) to about 50° C.; and
d) optionally filtering the solution of step (iii) on celite; and
e) cooling the solution of step (iv) further to about 5° C.; and
f) recovering the solid precipitated in step (v) by conventional methods to afford pure rifaximin.

In yet another aspect, the present invention relates to a process for the preparation of Rifaximin comprising the steps of:
a) providing rifaximin in a solvent or mixture of solvents; and
b) heating the suspension of step (i) to about 65° C. to obtain a solution; and
c) cooling the solution of step (ii) to about 50° C.; and
d) optionally filtering the solution of step (iii) on celite; and
e) cooling the solution of step (iv) further to about 5° C.; and
f) recovering the solid precipitated in step (v) by conventional methods to afford pure rifaximin.

In yet another aspect, the present invention relates to novel crystalline form of Rifaximin obtained by the processes of the present invention, characterised by powder X-ray diffraction pattern having characteristic peaks at about 5.9, 7.3, 7.9 and 8.6+0.2° 2θ.

DETAILED DESCRIPTION OF THE INVENTION

Figure 1:
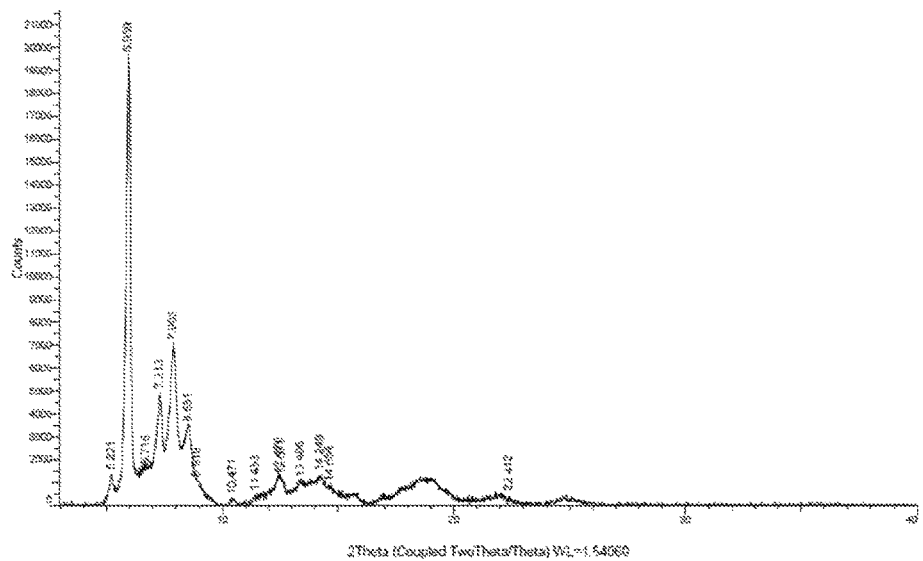
FIG. 1: Represents X-ray powder diffraction pattern of Rifaximin novel crystalline Form G

The present invention relates to improved processes for the preparation of Rifaximin. Particularly, the present invention relates to improved processes for the preparation of Rifaximin from Rifamycin O and S.

In one embodiment, the present invention provides an improved process for the preparation of Rifaximin of Formula I which comprises:
  a) bromination of rifamycin S in a suitable solvent in the presence of an organic base,
  b) isolating 3-bromorifamycin S with a strong acid in a suitable solvent,
  c) reacting 3-bromorifamycin S with 2-amino-4-methyl pyridine in a su able solvent,
  d) treating the reaction mixture with ascorbic acid,
  e) optionally washing the organic layer with an acid, removing the solvent,
  f) isolating crude Rifaximin, and
  g) purifying the crude Rifaximin obtained in step f) to obtain substantially pure Rifaximin.

According to the present invention the term "suitable solvent" in the above steps a, b and c is selected from "polar protic solvents" such as water; "polar aprotic solvents" such as dimethylsulfoxide, dimethylacetamide, dimethyl formamide and the like; "nitrile solvents" such as acetonitrile, propionitrile, butyronitrile and isobutyronitrile and the like; "ether solvents" such as di-tert-butylether, diethylether, diisopropyl ether, 1,4-dioxane, methyltert-butylether, ethyl tert-butyl ether, tetrahydrofuran and dimethoxyethane; "alcohol solvents" such as methanol, ethanol, n-propanol, isopropanol, n-butanol and t-butanol and the like; "chloro solvents" such as methylene chloride, ethylene dichloride, carbon tetra chloride, chloroform, chloro benzene and the like; "hydrocarbon solvents" such as benzene, toluene, xylene, heptane, hexane and cyclohexane; "ketone solvents" such as acetone, ethyl methyl ketone, diethyl ketone, methyl tert-butyl ketone, isopropyl ketone and the like; "esters solvents" such as ethyl acetate, methyl acetate, n-butyl acetate, isobutyl acetate, sec-butyl acetate, isopropyl acetate and the like; and their mixtures thereof.

The term "base" used in the present invention is selected from organic base such as diethylamine, trimethylamine, triethylamine, triethanolamine, di-n-propylamine, diisopropylethylamine, tert-butylamine, dimethylaniline, N-methylmorpholine, pyridine, dimethylaminopyridine or mixtures thereof.

As used herein the term "acid" refers to a strong acid which is selected from HCl, $H_2SO_4$, $H_3PO_4$, $HNO_3$, $Cl_2CCO_2H$, $Cl_3CCO_2H$, $F_3CCO_2H$, $HCO_2H$, $HClO_4$ and mixtures thereof.

The isolation and purification of Rifaximin according to the present invention is carried out using conventional methods used for isolation of compounds known in the field.

The term "substantially pure Rifaximin" refers to Rifaximin having the purity greater than about 98% by weight, preferably greater than about 99% by weight, and more preferably greater than about 99.3% by weight.

In another preferred embodiment, the reaction of halogentation in step (a) is carried out at temperature of about −40° C. to about 10° C., preferably to about −1 $H_3CCOOH$, 0° C. to about 10° C.

In one embodiment, the present invention provides an improved process for the preparation of Rifaximin of Formula I which comprises:
  a) bromination of rifamycin S in a suitable solvent in the presence of an organic base at a temperature of 0-10° C.,
  b) isolating 3-bromorifamycin S with a strong acid in a suitable solvent,
  c) reacting 3-bromorifamycin S with 2-amino-4-methyl pyridine in a suitable solvent,
  d) treating the reaction mixture with ascorbic acid,
  e) optionally washing the organic layer with an acid, removing the solvent,
  f) isolating crude Rifaximin, and
  g) purifying the crude Rifaximin obtained in step f) to obtain substantially pure Rifaximin.

In a most preferred embodiment, the present invention provides an improved process for the preparation of 3-bromorifamycin-S which comprises:
  a) dissolving Rifamycin S in toluene,
  b) cooling the reaction mixture to −10 to −5° C.,
  c) adding a mixture of ethanol bromine and pyridine the reaction mixture obtained in step b),
  d) isolating 3-bromorifamycin S after washing with aq.HCl.

In another most preferred embodiment, the present invention provides an improved process for the preparation of 3-bromorifamycin-S which comprises:
  a) dissolving Rifamycin S in ethylacetate
  b) cooling the reaction mixture to −10 to −5° C.
  c) adding a mixture of ethanol, bromine and pyridine to the reaction mixture obtained in step b)
  d) isolating 3-bromorifamycin S was after with aq.HCl.

In another most preferred embodiment, the present invention provides an improved process for the preparation of Rifaximin of Formula I which comprises:
  a) dissolving Rifamycin S in toluene,
  b) cooling the reaction mixture to −10 to −5° C.,
  c) adding a mixture of ethanol, bromine and pyridine to the reaction mixture obtained in step b),
  d) isolating 3-bromorifamycin S by washing with aq.HCl,
  e) dissolving the 3-bromorifamycin S obtained in step d) in dichloromethane,
  f) adding 2-amino-4-methyl pyridine,
  g) adding ascorbic acid to the reaction mixture in step f),
  h) washing the organic layer with aq.HCl to give crude Rifaximin
  i) recrystallizing the crude Rifaximin obtained in step h) using 30% aqueous Ethanol to substantially pure Rifaximin.

In yet another most preferred embodiment, the present invention provides an improved process for the preparation of Rifaximin of Formula I which comprises:
  a) dissolving Rifamycin S in ethylacetate,
  b) cooling the reaction mixture to −10 to −5° C.,
  c) adding a mixture of ethanol, bromine and pyridine to the reaction mixture obtained in step b),
  d) isolating 3-bromorifamycin S with aq.HCl and ethylacetate, e) dissolving the 3-bromorifamycin S obtained in step d) in dichloromethane, f) adding 2-amino-4-methyl pyridine, g) adding ascorbic acid to the reaction mixture in step f), h) isolating crude Rifaximin with aq.HCl.

i) recrystallizing the crude Rifaximin obtained in step h) using 30% aqueous Ethanol to get substantially pure Rifaximin.

In yet another preferred embodiment, the present invention provides an improved process for the preparation of Rifaximin comprising the steps of:

a) reacting rifamycin S with 2-amino-4-methylpyridine in the presence of iodine, acetic acid and acetonitrile at about 30° C. for about 30 hours; and b) obtaining resulted rifaximin as residue; and c) suspending rifaximin residue in a solvent or mixture of solvents; and d) heating the suspension of step (c) to about 75° C. to obtain a solution; and e) cooling the solution of step (d) to about 45° C.; and f) optionally seeding the solution of step (e) with seed crystal; and g) cooling the suspension of step (f) further to about 25° C. for about 2 hours; and h) cooling the mass of step (g) further to about 5° C. for about 3 hours; and i) recovering the solid precipitated in step (h) by conventional methods; and j) drying the solid obtained in step (i) at about 50° C. for about 10 hours to afford pure rifaximin.

In a preferred embodiment, the reaction time in step (a) can be from about 20 to about 35 hours, preferably from about 28 to about 30 hours is optimum.

The solvents that can be used in step (c) include but are not limited to water, alcohols selected from methanol, ethanol, isopropyl alcohol, n-butanol, isobutyl alcohol, amyl alcohol, tertiary butyl alcohol or a mixture thereof at various proportions without limitation. Preferably a mixture of ethanol and water is being used.

As used herein a mixture of solvents refers to a composition comprising more than one solvent.

Preferably, in step c) the residue is suspended in a mixture of solvents such as ethanol and water comprising at least 95% ethyl alcohol per volume.

The mixture of ethanol and water used for preparing a solution of rifaximin in step (c) typically may contain at least 95%, 96%, 97%, 97.5%, 98% or 99% of ethanol per volume.

The volumetric ratio in mixture of ethyl alcohol and water can be from about 1:1 to 1:9. Preferably a ratio of 1:1 is used.

The temperature for obtaining solution in step (d) can be from about 60° C. to about 75° C. or the boiling point of the solvent or mixture of solvents used, preferably from about 65° C. to about 75° C.

The solution of step (e) can be cooled from about 40° C. to about 60° C., preferably to about 50° C.

In step (g) the reaction mass of step (f) is further cooled from about 20° C. to about 35° C., preferably to about 25° C. and maintained for a period of about 30 mins to about 4 hours, preferably for about 2 hours.

In step (h), the reaction mass of step (g) is further cooled from about −10° C. to about 10° C., preferably to about 5° C. and maintained for a period of about 30 mins to about 5 hours, preferably for about 3 hours.

The solid rifaximin is precipitated according to any known technique. Typically, the solids resulting from the reaction are precipitated by cooling the solution. Precipitating the solid is for example performed by cooling the solution to a temperature comprised between 0° C.-15° C. preferably between 5° C.-10° C. in a period of time comprised between 15-60 minutes preferably between 25-40 minutes.

In preferred embodiments the solution is cooled to 5° C. in 60 minutes.

In another embodiment, the present invention provides a process for the preparation of rifaximin comprising the steps of:

a) providing rifaximin in a solvent or mixture of solvents; and b) heating the suspension of step (i) to about 65° C. to obtain a solution; and c) cooling the solution of step (ii) to about 50° C.; and d) optionally filtering the solution of step (iii) on celite; and e) cooling the solution of step (iv) further to about 35° C. for about 3 hours; and f) cooling the mass of step (v) further to about 5° C. for about 12 hours; and g) recovering the solid precipitated in step (vi) by conventional methods to afford pure rifaximin.

The solvents that can be used in step (i) include but are not limited to water, alcohols selected from methanol, ethanol, isopropyl alcohol, n-butanol, isobutyl alcohol, amyl alcohol, tertiary butyl alcohol or a mixture thereof at various proportions without limitation. Preferably a mixture of ethanol and water is being used.

The temperature for obtaining solution in step (ii) can be from about 55° C. to about 70° C. or the boiling point of the solvent or mixture of solvents used, preferably from about 60° C. to about 65° C.

The solution in step (iii) is cooled from about 45° C. to about 55° C., preferably to about 50° C.

The reaction mass of step (v) is further cooled from about 20° C. to about 35° C., preferably to about 35° C. and maintained for a period of about 30 mins to about 5 hours, preferably for about 3 hours.

The reaction mass of step (vi) is further cooled from about −10° C. to about 10° C., preferably to about 5° C. and maintained for a period of about 2 hours to about 15 hours, preferably for about 12 hours.

The precipitated solids are recovered by conventional method such as filtration or centrifugation and the recovered solid rifaximin is washed.

Washing usually includes washing with a mixture of ethyl alcohol and water.

In an embodiment, the mixture of ethyl alcohol and water in a volumetric ratio 1:1 is being used. However other ratios are also contemplated within this present invention.

After washing, the rifaximin can be dried according to any appropriate method.

The process is shown in the scheme given below:

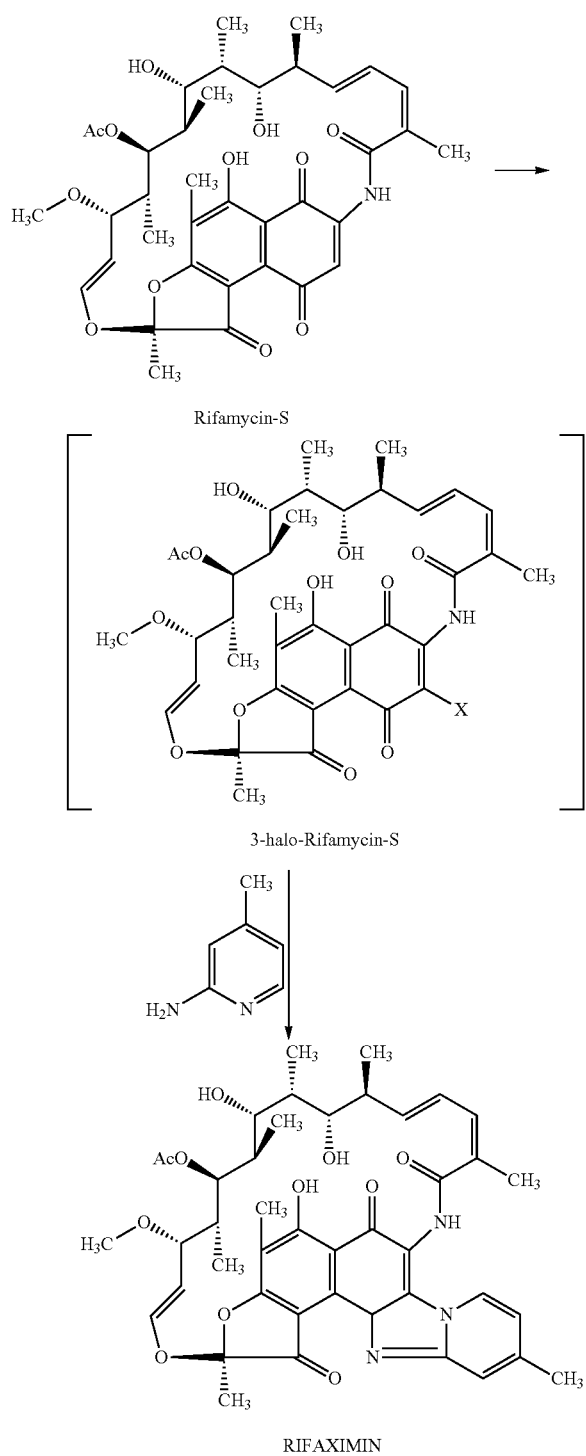

The Rifaximin obtained by the above described processes of present invention may be dried under vacuum or under normal pressure, in the presence of drying agents or not and at any appropriate temperature. Preferably, drying is performed under vacuum at 50° C. and for a period from about 5 hours to about 15 hours preferably 10 hours.

Advantageously, the processes of present invention provides Rifaximin with high yield and purity.

Preferably, the yield of the Rifaximin obtained by the processes described above is greater than about 80%, or more, more preferably, the yield is greater than about 85%, most preferably, the yield is greater than about 90%, or more, by weight.

Advantageously, the Rifaximin obtained by the processes described above has at purity preferably purity of at least about 99.5%, or more preferably at least about 99.9 area % and impurities less than about 1% more preferably less than about 0.5%, and most preferably less than about 0.1% by HPLC.

The improved methods of the present invention provides Rifaximin with fewer impurities, in preferred embodiments, the processes of the present invention results in a crystalline polymorph which possesses advantageous physicochemical properties which render its processing as a medicament beneficial.

In one of the embodiment, the novel crystalline form of Rifaximin obtained by the processes of the present invention was characterised by powder X-ray diffraction pattern having characteristic peaks at about 5.9, 7.3, 7.9 and 8.6±0.2° 2θ. The said novel crystalline Form obtained herein is designated as Form G.

The crystalline Form of Rifaximin obtained by the processes of the present invention was further characterized by powder X ray diffraction pattern having characteristic peaks at about 5.2, 5.9, 6.6, 7.3, 7.9, 8.6, 12.5, 14.2, 18.5 and 19.1±0.2° 2θ which is substantially same as FIG. 1.

Figure 2:
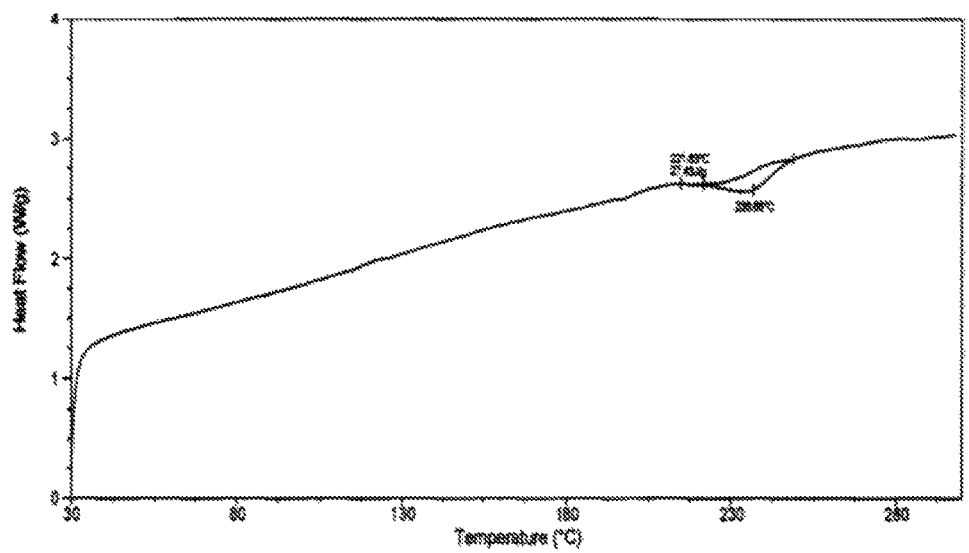
FIG. 2: Represents Differential Scanning calorimetry (DSC) endotherm peak of Rifaximin novel crystalline Form G.

The crystalline Form G of Rifaximin obtained by the processes of the present invention was further characterized by differential scanning calorimetry (DSC) having endothermic peak at 236.68° C. with onset temperature of 221.6° C. which is substantially same as FIG. 2.

The crystalline Form G of Rifaximin obtained by the processes of the present invention was characterised by powder X-ray diffractography using Powder XRD make: Bruker model D2 Phaser Goniometer type theta—2 theta; X-ray source: Copper Kα; Detector: Lynx Eye Detector.

Rifaximin samples data was collected using PMMA holder with the scan parameter details as follows:

2θ range: 3-40°; Step size: 0.012; Time for step: 72 S; Generator KV: 30; Generator Ma: 10; Spinner: 15 rpm;

Method of Analysis:

Sample preparation: If required sample is finely grind using a mortar and pestle, then pack the sample in a suitable sample holders. Selection of the sample holder depends on the sample quantity.

Ex: a) 25 mm/49 mm dia, sample holders made up of PMMA will be used if the sample quantity is more than 500 mg.

b) 8.5 mm dis. Silicon zero background holders will be used if the sample quantity is less than 100 mg.

The crystalline Form of rifaximin obtained by the processes of the present invention was further characterised by differential scanning calorimetry (DSC) using instrument make: TA instruments, software: Universal analysis, Model: Q100.

Method of Analysis:

Sample preparation: Weigh accurately about 2.0-5.0 mg of test sample and transfer into aluminium hermetic pan, close with lid and seal with a crimper. Hold it in the sample compartment with furnace temperature programme: 30° C. to 300° C. and at ramp rate of 5° C./min.

Rifaximin used herein as starting material in one of the embodiment of present invention can be made from rifamycin S or rifamycin O or obtained from any of processes reported in the literature for example crude rifaximin can be prepared as per example 4 of U.S. Pat. No. 4,557,866.

Rifaximin used herein can be crystalline or amorphous or mixture thereof.

The starting compounds rifamycin S or rifamycin O used herein the processes of rifaximin can be obtained from any of the processes reported in the literature and can be of any polymorph or mixture of polymorphs.

The following examples describes the nature of the invention and are given only for the purpose of illustrating the present invention in more detail and are not limitative and relate to solutions which have been particularly effective on a bench scale.

EXAMPLES

Example 1

5 g of Rifamycin S, 3.1 gms of 2-amino-4-methyl pyridine, 0.45 g of iodine, 1.65 ml of acetic acid and 20 ml of acetonitrile were charged in a clean and dry round bottom flask followed by stirring the resultant reaction mixture at about 30° C. for about 30 hours. The reaction progress was monitored by TLC, after completion of reaction, the reaction mass was quenched by adding a mixture of 4.0 g of ascorbic acid dissolved in 20 ml of water. The resultant reaction suspension was stirred at about 25° C. for about 15 mins. 25 ml of dichloromethane was charged and stirred for about 15 mins. followed by separation of organic and aqueous phases. The aqueous phase was extracted with 25 ml of dichloromethane followed by separation of organic and aqueous phases. The organic phases were combined and distilled at below about 50° C. to yield Rifaximin as residue. 11.25 ml of purified water and 11.25 ml of ethanol were charged to the residue and stirred at about 30° C. for about 15 mins. The resultant reaction suspension was heated to about 75° C. and stirred for about 30 mins. The resultant reaction solution further cooled to about 25° C. and stirred for about 2 hours followed by further cooling to about 5° C. for about 3 hours. The solid precipitated was filtered and the solid was washed with a mixture of 2.5 ml of ethanol and 2.5 ml of purified water. The solid obtained was dried at about 50° C. for about 10 hours to afford 3 g. of Rifaximin as crystalline form.

Purity by HPLC: 99.85 area %.

Example 2

10 g of Rifamycin O and 4.3 g of 2-amino-4-methyl pyridine, and (25.8 ml) of purified water and (19.4 ml) of ethanol were charged into a clean and dry R.B. Flask followed by heating to about 45° C. The resultant suspension was stirred at about 45° C. for about 8 hours. The resultant solution was cooled to about 25-35° C. and stirred at 25-35° C. for about 12 hours. The solid separated was filtered and washed the solid with (3.2 ml) of ethanol and (3.2 ml) of purified water. The solid obtained was dried at about 50° C. for about 10 hours to afford 9 g of rifaximin as crystalline form.

Purity by HPLC: 99.89 area %.

Example 3

10 g of Rifaximin, (71.0 ml) of ethanol and (30.6 ml) of purified water were charged into a clean and dry R.B. Flask followed by heating to about 65° C. The resultant suspension was stirred at about 65° C. for about 2 hours. The resultant solution was cooled to about 50° C. and filtered through a microfilter and seeded with seed crystal. The solution was further cooled to about 35° C. and stirred at about 30° C. for about 3 hours. The resultant mass was further cooled to about 5° C. and stirred for about 12 hours. The solid separated was filtered and the solid was washed with (4.8 ml) of ethanol and (1.6 ml) of purified water. The solid obtained was dried at about 50° C. for about 10 hours to afford 9.5 g of rifaximin as crystalline form.

Purity by HPLC: 99.87 area %.

Example 4

10 g of Rifamycin S was charged into toluene and cooled to −10 to −5° C. and to this mixture of ethanol and 4.0 gm of Molecular bromine and 4.0 gm of pyridine was added slowly then maintained the reaction mass for one hour at same temperature and material is isolated by using 0.5% Aq HCl washing of the reaction medium and filtration of resulting solid gives 3-Bromorifamycin-S. The obtained solid was added to dichloromethane along with 3.3 gm of 2-Amino-4-methyl pyridine and stirring continued for 4-5 hours then charged Ascorbic acid and maintained for 5-6 hours gives Rifaximin crude compound which is isolated by washing the dichloromethane layer within 0.5% Aq. HCl solution followed by distillation of dichloromethane and isolated the material by using 30% Aq. Ethanol solution with recrystallization technique gives pure 7.0 gm of Rifaximin.

HPLC Purity: 99.78; Imp-D&H: 0.03.

Example 5

10 g of Rifamycin S was charged into ethylacetate (100 ml) and cooled to −10 to −5° C. To this reaction mixture was added slowly of mixture ethanol (50.0 ml), 4.0 gm of molecular bromine and 4.0 gm of pyridine and maintained the reaction mass for one hour at same temperature to give 3-Bromorifamycin-S. The material was isolated by using 0.5% Aq HCl washing of the reaction medium and filtration of resulting solid gives 3-Bromorifamycin-S. The solid obtained was added to a mixture of dichloromethane (100.0 mL) and 3.3 gm of 2-amino-4-methyl pyridine and stirring continued for 4-5 hours at 5-15° C. Then 3.0 gm of Ascorbic acid was charged to the reaction mixture and maintained for 5-6 hours at 5-15° C. to give crude Rifaximin compound which was isolated by washing the with 0.5N HCl (2×30.0 mL) solution followed by distillation of dichloromethane and isolated the material by using 30% aq. Ethanol solution with recrystallization technique to give substantially pure Rifaximin (7.0 g).

HPLC Purity: 99.61; Imp-D&H: 0.13.

We claim:

1. A process for the preparation of crystalline Form G of Rifaximin of Formula I chracterised by X-ray powder diffraction peaks at 5.2, 5.9, 6.6, 7.3, 7.9, 8.6 and 12.5±0.2° 2θ which wherein the process comprises:

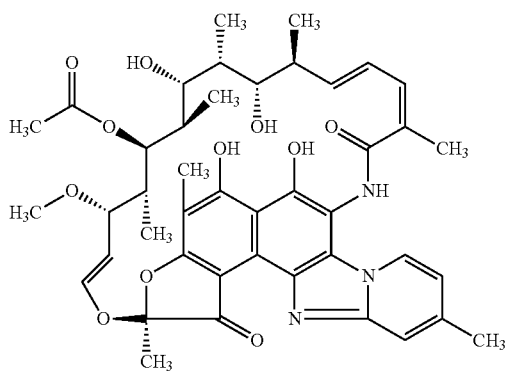

Formula I a) treating rifamycin S with Bromine in a suitable solvent in the presence of a base, at temperature ranging between −20 to 10° C.,
b) optionally isolating 3-bromorifamycin S with an acid in a suitable solvent,
c) reacting 3-bromorifamycin S with 2-amino-4-methyl pyridine in a suitable solvent,
d) treating the reaction mixture with ascorbic acid,
e) isolating pure Rifaximin,
f) crystallising the pure Rifaximin obtained in step e) to get crystalline Form G of Rifaximin.

2. The process according to claim 1, wherein the suitable solvent is selected from nitrile solvents as acetonitrile, propionitrile or alcohol solvents as methanol, ethanol, n-propanol, isopropanol, n-butanol and t-butanol or hydrocarbon solvents as toluene, xylene, or esters solvents as ethyl acetate, methyl acetate, or water or mixtures thereof.

3. The process according to claim 1, wherein the suitable base in step (a) is selected from pyridine, dimethylaminopyridine, 2-amino-4-methyl pyridine and acid in step (b) is selected from HCl, $H_2SO_4$, $HNO_3$ and $H_3CCOOH$.

4. The process according to claim 1, wherein step (f) of crystallising Rifaximin comprising the steps of:
   a) providing Rifaximin in a suitable solvent or mixture of solvents;
   b) heating the suspension of step (a) and stirring the solution at temperature 20-85° C.;
   c) optionally filtering the solution of step (b) on celite or on carbon bed;
   d) cooling the solution of step (c) to 30-50° C.;
   e) cooling the solution of step (d) further to −5-20° C.; and
   f) recovering the pure Rifaximin Form G chracterised by X-ray powder diffraction peaks at 5.2, 5.9, 6.6, 7.3, 7.9, 8.6 and 12.5±0.2° 2θ.

5. The process according to claim 4, wherein the solvent in step (a) is selected from water, alcohols selected from methanol, ethanol, isopropyl alcohol, n-butanol or mixture thereof.

6. Crystalline Rifaximin designated as Form (characterised by
   a. X-ray powder diffraction pattern having characteristic diffraction angle peaks at 5.2, 5.9, 6.6, 7.3, 7.9, 8.6 and 12.5±0.2° 2θ:
   b. DSC isothermal peak ranging between 220-240° C.

* * * * *